United States Patent [19]

Dessau

[11] Patent Number: 4,517,402
[45] Date of Patent: May 14, 1985

[54] SELECTIVE SORPTION OF LINEAR ALIPHATIC COMPOUNDS BY ZEOLITES

[75] Inventor: Ralph M. Dessau, Edison, N.J.

[73] Assignee: Mobil Oil Corporation, New York, N.Y.

[21] Appl. No.: 490,910

[22] Filed: May 2, 1983

Related U.S. Application Data

[63] Continuation-in-part of Ser. No. 307,045, Sep. 30, 1981, abandoned, which is a continuation-in-part of Ser. No. 105,190, Dec. 19, 1979, Pat. No. 4,309,281.

[51] Int. Cl.³ .............................................. C07C 7/13
[52] U.S. Cl. ................................. 585/820; 208/310 Z
[58] Field of Search ..................... 208/310 Z; 585/820

[56] References Cited

U.S. PATENT DOCUMENTS

| 3,258,417 | 6/1966 | Hess et al. | 208/26 |
| 3,699,182 | 10/1972 | Cattanach | 208/310 Z X |
| 3,709,979 | 1/1973 | Chu | 423/328 |

Primary Examiner—G. L. Kaplan
Assistant Examiner—W. T. Leader
Attorney, Agent, or Firm—A. J. McKillop; M. G. Gilman; L. G. Wise

[57] ABSTRACT

A process for selective separation of a linear aliphatic compound in admixture with at least one non-linear hydrocarbon compound, said compounds having a critical dimension of less than 6.8 Angstrom Units for sorption, which comprises contacting the mixture with zeolite ZSM-11, said zeolite being characterized by a silica:alumina mole ratio of at least 12, to effect selective sorption of said linear aliphatic compound by said zeolite.

8 Claims, No Drawings

SELECTIVE SORPTION OF LINEAR ALIPHATIC COMPOUNDS BY ZEOLITES

CROSS-REFERENCE TO RELATED APPLICATION

This is a continuation-in-part of application Ser. No. 307,045, filed Sept. 30, 1981, now abandoned which is a continuation-in-part of application No. 105,190, filed Dec. 19, 1979, now U.S. Pat. No. 4,309,281.

BACKGROUND OF THE INVENTION

1. Field of the Invention

This invention relates to a sorptive separation process using crystalline zeolites. More specifically, the invention pertains to the selective sorptive separation of linear aliphatic hydrocarbons and derivatives thereof in admixture with non-linear organic compounds. The zeolites found to be useful in the present process are those having a silica/alumina mole ratio of greater than about 12, and in particular zeolite ZSM-11.

2. Description of the Prior Art

Certain porous substances such as silica gel, activated char, and zeolites, have certain selective adsorption characteristics useful in resolving a hydrocarbon mixture into its component parts. Thus, silica gel is selective in removing aromatic hydrocarbons from non-aromatic hydrocarbons and activated chars are useful in separating olefins from mixtures with paraffins. Similarly, it is well known in the art that certain crystalline zeolites can be used to separate certain hydrocarbons from feed mixtures.

The selective sorption properties of zeolites are generally known and have been described, for instance, in U.S. Pat. Nos. 2,850,549; 2,866,835; 3,037,338 and 3,218,367. The general sorption properties of zeolites have been disclosed in some of the earlier patents on the zeolites per se, namely U.S. Pat. Nos. 2,882,243 and 2,882,244. Additionally, there are numerous literature references, especially those of Barrer, which deal extensively with the sorption properties of crystalline zeolites. Generally speaking, crystalline zeolites are shape-selective in that they will admit molecules of specific geometry while excluding other molecules.

The separation of normal paraffins from branched chained paraffins for example can be accomplished by using a type A zeolite which has pore openings from 3 to about 5 Angstroms. Such a separation process is disclosed in U.S. Pat. Nos. 2,985,589 and 3,201,491. These adsorbents allow a separation based on the physical size differences in the molecules by allowing the smaller or normal hydrocarbons to be passed into the cavities within the zeolitic adsorbent, while excluding the larger or branched chain molecules. U.S. Pat. Nos. 3,265,750 and 3,510,423 for example, disclose processes in which larger pore diameter zeolites such as the type X or type Y structured zeolites can be used to separate olefinic hydrocarbons from non-olefinic hydrocarbons. Processes to separate straight chain hydrocarbons from a mixture of straight chain and non-straight chain hydrocarbons using a molecular sieve selective adsorbent are described in U.S. Pat. Nos. 3,619,409 and 3,619,416.

Additionally, such crystalline zeolites will exclude aromatics such as benzene while admitting normal hexane. It has been disclosed in British Pat. No. 600,453 that zeolites can be employed as selective sorption agents and that such zeolites will sorb polar molecules in preference to less polar molecules. A method for selectively sorbing a compound of low polarity in admixture with a compound of greater polarity using a zeolite is disclosed in U.S. Pat. No. 3,732,326. The latter patent discloses use of zeolite ZSM-5 for selectively sorbing hydrocarbons of low polarity in admixture with compounds of greater polarity such as water, alcohols, acids, aldehydes and halogen-substituted compounds.

U.S. Pat. No. 3,723,302 discloses a process for separating olefins from a feed stream containing olefins and paraffins using type X or type Y zeolites. A process for the separation of olefins from a hydrocarbon feed mixture using a zeolite adsorbent is disclosed in U.S. Pat. No. 3,969,223. A process for the separation and recovery of hydrocarbons selected from paraffins or olefins or both from admixture with aromatic hydrocarbons using aluminum-deficient mordenite is disclosed in U.S. Pat. No. 3,485,748.

The separation of xylene isomers has received a great deal of attention. This interest is generally attributed to the usefulness of para-xylene in the manufacture of terephthalic acid which is an intermediate in the manufacture of synthetic fibers such as "Dacron", "Mylar" and "Terylene". Mixtures of xylene isomers generally contain a concentration of about 24 weight percent para-xylene in the equilibrium mixture. Processes to separate xylene isomers include low temperature crystallization, fractional distillation, selective sulfonation with subsequent hydrolysis and selective solvent separation. Such processes, however, have involved high operation costs and usually result in a limited yield.

U.S. Pat. No. 3,868,429 discloses a method to separate xylene isomers by using activated carbon.

The separation of xylene isomers by the use of faujasite zeolites (type X and type Y zeolites) has been extensively studied. The use of type X and type Y zeolites in xylene isomer separation and similar separations is disclosed in U.S. Pat. Nos. 3,114,782; 3,126,425; 3,133,126; 3,558,730; 3,558,732; 3,626,020; 3,663,638; 3,665,046; 3,686,342; 3,943,183 and 4,051,192.

U.S. Pat. No. 3,793,385 discloses a process for the separation of aromatic isomers, more particularly xylene isomers, by using zeolite beta.

U.S. Pat. No. 3,724,170 discloses chromatographic separation of $C_8$ aromatic mixtures over zeolite ZSM-5. U.S. Pat. No. 3,699,182 discloses use of zeolite ZSM-5 in a process for selective separation of biphenyls from mixtures containing same and para-disubstituted aromatic isomers from mixtures containing same. British Pat. No. 1,420,796 shows use of zeolite ZSM-5 for adsorptive separation of p-xylene and ethylbenzene from a mixture comprised of the xylene isomers and ethylbenzene.

Catalytic dewaxing of gas oil fractions over the shape selective zeolites ZSM-5, ZSM-11, ZSM-12, ZSM-35 and ZSM-38 is taught in U.S. Pat. Nos. 3,980,550 and 4,149,960.

The ZSM-5 class of crystalline zeolites has been shown to be catalytically selective. This shape selectivity can be further enhanced by the use of very large crystals, impregnation with Mg and P to reduce zeolite pore openings and coke selectivation. These modified zeolite catalysts have been very effective in such reactions as selective toluene disproportionation which yields predominantly paraxylene as the product and toluene-ethylene alkylation yielding primarily para-ethyltoluene.

ZSM-5 type zeolites possess pore openings intermediate in size between the small pore and the large pore zeolites. It sorbs at room temperature straight chain monomethyl-substituted paraffins and monocyclic hydrocarbons at significantly faster rates than those containing dimethyl-substituted or quaternary carbon atoms, and it excludes molecules with critical dimensions larger than that of 1,3,5-trimethylbenzene. Zeolite ZSM-5 has a pore system which differentiates catalytically molecules having a straight chain, a methyl substitution and a dimethyl substitution. The catalytic properties of ZSM-5 are further elucidated by Chen and Garwood in *Some Catalytic Properties of ZSM-5, a New Shape Selective Zeolite*, JOURNAL OF CATALYSIS, Vol. 52, No. 3 (May 1978).

Satterfield and Cheng, *Liquid Sorption Equilibrium of Selected Binary Hydrocarbon Systems in Type Y Zeolites*, AICHE JOURNAL, Vol. 18, No. 4, p. 720, July 1972 and Satterfield and Smeets, *Liquid Sorption Equilibria of Selected Binary Paraffin Systems in NaY Zeolite*, AICHE JOURNAL, Vol. 20, No. 3, p. 618, May 1974, teach that on zeolite Y aromatic compounds are selectively adsorbed over paraffins and smaller compounds are adsorbed in preference to larger compounds. Contrary to said teaching, the zeolites for use in the instant invention yield the unexpected results of selective adsorption of paraffins over aromatics and selective adsorption of higher molecular weight molecules over smaller members of the same family.

SUMMARY OF THE INVENTION

A process has been discovered for selective separation of a linear aliphatic compound in admixture with at least one nonlinear compound, said compounds having a critical dimension of less than 6.8 Angstrom Units for sorption, which comprises contacting the mixture of paraffins with a zeolite ZSM-11, said zeolite being characterized by a silica:alumina mole ratio of at least 12, to effect selective sorption of said linear paraffin by said zeolite. The process is useful for separating paraffinic and olefinic isomers. For instance, n-hexane is selectively sorbed from a solution containing its methyl pentane isomer with a selectivity factor of about 14. The crystalline zeolite consisting essentially of H-ZSM-11 has medium pore constraint index and can give selectivity superior to H-ZSM-5 in certain processes.

DESCRIPTION OF SPECIFIC EMBODIMENTS

The process of this invention is concerned with the separation of organic compound mixtures by the selective sorption properties of certain ZSM-11 zeolite compositions characterized by a silica to alumina mole ratio of at least 12 and a Constraint Index (C.I.) within the approximate range of greater than 2 to about 12, (typically C.I.=8.7).

The zeolites useful herein possess the ability to selectively sorb straight chain aliphatic compounds from mixtures thereof with more highly substituted and/or branched organic compounds of the same chemical type or class e.g. olefin from olefin, paraffin from paraffin, etc. either as substituted or unsubstituted hydrocarbons. It is understood herein that individual "chemical types or classes" of compounds will be defined as paraffins, olefins, benzene-substituted paraffins, benzene-substituted olefins, heteroatom-substituted paraffins or heteroatom-substituted olefins. Heteroatom compounds, both aromatic and non-aromatic, will contain substituents selected from the group consisting of halogen (e.g. F, Cl, Br and I), sulfur-containing groups (e.g. thiols, disulfides, thioacids and thioesters), oxygen-containing groups (e.g. alcohols, ketones, esters and acids) and nitrogen-containing groups (e.g. amines, imines, nitriles and amides).

Non-limiting examples of aliphatic hydrocarbons (e.g., paraffins and olefins) are listed below in terms of (a) unsubstituted linear hydrocarbons which will be sorbed by the present process in favor of (b) branched non-linear hydrocarbons in mixture (a+b) therewith.

| (a) | (b) |
| --- | --- |
| n-butane | isobutane |
| n-hexane | 2-methylpentane |
| n-octane | 2,5-dimethylhexane |
| 2-hexene | 4-methyl-2-pentene |

Non-limiting examples of heteroatom-substituted compounds are listed below in terms of (c) lesser substituted heteroatom compounds which will be sorbed by the present process in favor of (d) more highly substituted and/or branched heteroatom compounds in mixture (c+d) therewith:

| (c) | (d) |
| --- | --- |
| n-propyl alcohol | isopropyl alcohol |
| 2-methyl-1-butanol | 2-methyl-2-butanol |
| n-butyl alcohol | tert-butyl alcohol |

Non-limiting examples of benzene-substituted paraffins and olefins are listed below in terms of (e) lesser substituted aromatic hydrocarbons which will be sorbed by the present process in favor of (f) more highly substituted and/or branched aromatic hydrocarbons in mixture (e+f) therewith:

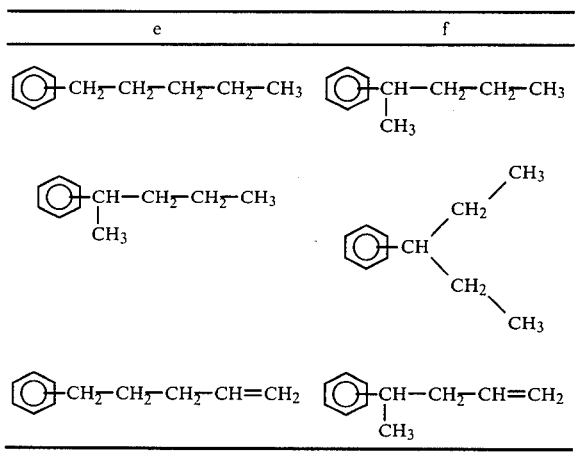

ZSM-11 type zeolites possess the ability to selectively sorb waxy paraffinic compounds such as, for example, waxy linear paraffins or, in general, mixed waxy paraffinic compounds from mixtures thereof with stocks containing other paraffinic compounds, such as, for example, crude oils, heavy oils, distillate oils and lube base oil stocks. Utilizing the zeolites of the present invention with crude oils, heavy oils, distillate oils and lube base stocks can be quite useful in the dewaxing of such oils via the selective sorption and separation of waxy paraffinic compounds. Thus, such paraffinic compounds can be selectively removed to such an extent so as to improve low temperature properties of the oil, i.e. increase its fluidity by reducing pour point. The paraffins removed from such oils include straight-chain and branched-chain hydrocarbons of from about 14 to 50 carbon atoms per molecule. Heavy oils and lube base oils include vacuum and/or hydrotreated gas oils. Distillate oils for use herein include, typically, those containing $C_{10}$ to $C_{20}$ hydrocarbons. Selectivity for one component over another in a mixture can be determined by the relative size differential therebetween as favored for sorption by the particular zeolite used. A significant factor in determining which compounds will be sorbed to any extent, either selectively from a mixture or individually, by the zeolites for use herein is the critical dimension of the compound. For the zeolites herein utilized, the compounds must have a critical dimension of 6.8 Angstrom Units or less to be sorbed. Therefore, to benefit from the selective sorption process herein claimed, both or all components of the mixture will have a critical dimension of 6.8 Angstroms or less.

Utility of the zeolites for use herein is illustrated in Table 1. Table 1 gives competitive selective sorption properties for a mixture comprising a normal organic compound, e.g. n-hexane, and more highly branched organic compound, e.g. 3-methylpentane in the presence of various zeolites, some of which are useful herein. As can be seen from Table 1, ZSM-5 and ZSM-11 show much greater preference for the sorption of certain compounds as compared to zeolite having a Constraint Index outside the range of greater than 2 to about 12, e.g. ZSM-12 and Mordenite. The ability of a particular zeolite to selectively sorb one compound in admixture with another is characterized by deriving the "selectivity" hereinafter defined.

TABLE 1

| COMPETITIVE SORPTIONS USING ZEOLITES | | |
| --- | --- | --- |
| Zeolite | Constraint Index | Selectivity |
| HZSM-5 | 8.3 | 12–21 |
| HZSM-11 | 8.7 | 14 |
| HZSM-12 | 2 | 2 |
| H—Mordenite (dealuminized Mordenite) | 0.4 | 0.7 |
| REY | 0.4 | less than 1 |

In adsorptive separation processes, an important factor that is used to determine the ability of a particular adsorbent to separate components of a feed mixture is the selectivity of the adsorbent for one component as compared to another component. The selectivity, as used throughout this specification, is defined as the ratio of the two components of the adsorbed or retained phase over the ratio of the same two components in the unadsorbed phase at equilibrium conditions. Selectivity is derived as follows: Selectivity =

$$S_{A,B} = \frac{(A \text{ adsorbed on zeolite})}{(B \text{ in solution})} \times \frac{(B \text{ adsorbed on zeolite})}{(A \text{ in solution})}$$

where A and B are the two components of the feed represented in volume percentages.

The equilibrium conditions as defined herein are determined when the feed is contacted with a bed of adsorbent and no change in composition results after such contacting. In other words, there is no net transfer of material occurring between the unadsorbed and adsorbed phases.

As can be seen, where the selectivity of the two components approaches unity, there is no preferential adsorption of one component by the adsorbent because the ratio of the feed to the components in the adsorbed and unabsorbed phases is equal. As the value of $S_{A,B}$ becomes less or greater than unity, there is a preferential selectivity by the adsorbent for one of the two components. When comparing a selectivity of component A over component B, an $S_{A,B}$ larger than unity indicates preferential adsorption of component A within the adsorbent, while an $S_{A,B}$ less than unity would indicate that component B is preferentially adsorbed by the adsorbent.

The novel process of the instant invention involves contacting an organic compound mixture, existing either as a gas, liquid or mixed phase with a member of the class of zeolites of this invention for a period of time to selectively sorb a preferred compound within the internal pore structure of said zeolite. The components of the mixtures that are not sorbed are thus carried off. The compound sorbed is thereafter recovered from the internal pore structure of the zeolite by conventional desorbing techniques such as stripping. Although inert solvents are employed in static batch systems to carry out many of the experiments illustrating this invention, the novel process of this invention can also be conducted in flow type (continuous) systems, e.g. continuous chromatographic type operation. In such a flow type system, a hydrocarbon mixture is passed through a bed containing a member of the class of zeolites of the present invention. The preferred compound is adsorbed or retained in the bed, while the unadsorbed compound is removed. The processes of this invention can be conducted in the presence of polar, e.g. water or alcohol, or non-polar solvents. Thus, selective sorptions of the kind and type described herein can take place in the presence of water, i.e. in aqueous solution.

The temperature at which the novel process of this invention is conducted is not considered critical, so long as it is maintained below that required for chemical reaction to occur, e.g. below cracking temperature. The temperature should thus be maintained below about 150° C. when an acidic zeolite (e.g. one having an Alpha value greater than 10) is used. When a relatively non-acidic zeolite (e.g. one having a $SiO_2/Al_2O_3$ mole ratio of about 1000 or more, or one having been converted to the alkali metal-containing form by ion exchange) is used, then higher temperatures may be utilized such as up to about 400° C. Preferably, the processes of this invention can be conducted in the temperature range between ambient and about 150° C.

Obtaining even higher selectivities for the zeolites for this improved process can be accomplished by reducing the diffusional rate characterics of these zeolites. The diffusional rate characteristic is defined as the rate of which a zeolite, or other adsorbent, sorbs a particular hydrocarbon, e.g. hexane or o-xylene. Modification of the diffusional rate characteristics may be suitably effected by precoking. Another means of achieving desired lower diffusional rate characteristics is the use of large crystal size zeolite having a minimum crystal dimension of greater than about 0.5 micron. Generally, the crystal size should be in the approximate range of between about 0.5 micron and greater than about 250 microns, and preferably in the range of between about 0.5 micron and 250 microns. As used throughout this specification and claims, zeolites with crystal diameters of about 0.02 micron to about 0.5 micron will be designated as "small crystal size" and zeolites with crystal diameters greater than about 0.5 micron will be designated as "large crystal size".

Still another means of achieving desired lower diffusional rate characteristics is to incorporate, such as by cation exchange, bulky cations such as cesium or tetramethylammonium cations with the useful zeolites of this invention. Other cations which may be exchanged into the zeolite to affect lower diffusional rate characteristics and thereby increase selectivity thereof for the present process include $Na^+$, $H^+$, $Cu^{++}$, $K^+$, $Sr^{++}$ and similar cations. A correlation of sorption selectivity exhibited by the exchanged zeolite for use herein with the ionic radius of the cation involved may be demonstrated.

Silica/alumina mole ratio also has an effect on the sorption selectivity of the zeolites for use herein, especially where large polarity differences are involved. Thus, for example, H-ZSM-5 having a $SiO_2/Al_2O_3$ mole ratio of 1670 may have a selectivity from four to five times that of a H-ZSM-5 having a $SiO_2/Al_2O_3$ mole ratio of 75. Likewise, it has been found that steaming a zeolite useful herein will also increase selectivity thereof. For example, an unsteamed H-ZSM-5 may provide a selectivity factor of 3.2, while that same zeolite after having been steamed for 2 hours at 538° C. will provide a selectivity of as much as 7.3.

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is valuable in some instances to use zeolites having much higher silica to alumina mole ratios, i.e. 1600 and above. In addition, zeolites as otherwise characterized herein but which are substantially free of aluminum, i.e. having silica to alumina mole ratios up to and including infinity, are found to be useful and even preferable in some instances. Such "high silica" or "highly siliceous" zeolites are intended to be included within this description. Also to be included in this definition are the pure silica analogs of the useful zeolites of this invention, i.e. hving absolutely no aluminum (silica to alumina mole ratio of infinity). Thus, zeolites useful herein have silica to alumina mole ratios of between about 12 and infinity, preferably greater than about 200, more preferably greater than about 500, and even more preferably greater than about 1000. The ZSM-11 class of zeolites may contain, in addition to silica, the oxides of B, Cr, Fe or Ga.

The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e. 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

There also may be instances where the activity is so low (i.e. silica to alumina mole ratio approaching infinity) that the constraint index cannot be adequately measured, if at all. In such situations, Constraint Index is meant to mean the Constraint Index of the exact same substance (i.e. same crystal structure as determined by such means as x-ray diffraction pattern) but in a measureable form (i.e. aluminum containing form).

The "Constraint Index" is calculated as follows:

$$\text{Constraint Index} = \frac{\log_{10} \text{(fraction of hexane remaining)}}{\log_{10} \text{(fraction of 3-methylpentane remaining)}}$$

The Constraint Index approximates the ratio of the cracking rate constants for the two hydrocarbons. Constraint Index values for some typical materials are:

|  | CONSTRAINT INDEX |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Clinoptilolite | 3.4 |
| Beta | 0.6 |
| H—Zeolon (mordenite) | 0.4 |
| REY | 0.4 |
| Amorphous Silica-Alumina | 0.6 |
| Erionite | 38 |

The above-described Constraint Index is an important characteristic of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions of ZSM-5 type zeolites as to establish more than one value in the expected range of about 2 to 12. A crystalline ZSM-11 zeolite when identified by any combination of conditions within the testing definition set forth herein will typically be found to have a Constraint Index in the approximate range of about 8.5 to 9.0.

The preferred zeolite type for use herein is described in U.S. Pat. No. 3,709,979. That description, and in particular the X-ray diffraction pattern of said ZSM-11, is incorporated herein by reference. It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are unsuitable for use herein, possibly because the intra-crystalline free space is occupied by organic cations from the forming solution. They may be made suitable by calcination in an inert atmosphere, such as, for example, at about 538° C. for from about one hour to about 5 hours in a nitrogen or air atmosphere. If desired these zeolites may be base exchanged with suitable compounds, e.g. salts, to get desired cationic form, e.g. sodium, hydrogen, ammonium, etc. The presence of organic cations in the forming solution may not be absolutely essential to the formation of this type zeolite; however, the presence of these cations does appear to favor the formation of this special class of zeolite.

In a preferred aspect of this invention, the zeolites hereof are selected as those providing, among other things, a crystal framework density in the dry hydrogen form of not less than about 1.6 grams per cubic centimeter. It has been found that zeolites which satisfy all three of the discussed criteria are most desired for several reasons. The dry density for known structures may be calculated from the number of silicon plus aluminum atoms per 1000 cubic Angstoms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small mount of free space within the crystal, which might be expected to result in more stable structures.

This free space, however, is important as the focus of catalytic activity.

Crystal framework densities of some typical zeolites, including some which are not within the purview of this invention are:

|  | Void Volume | Framework Density |
| --- | --- | --- |
| Ferrierite | 0.28 cc/cc | 1.76 g/cc |
| Mordenite | .28 | 1.7 |
| ZSM-5, 11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite can be conveniently converted to the hydrogen form, generally by intermediate formation of the ammonium form as a result of ammonium ion exchange and calcination of the ammonium form to yield the hydrogen form.

The following examples will serve to illustrate the process of the invention without limiting same.

EXAMPLE 1

This example illustrates the preparation of small crystal size ZSM-11. A sodium silicate solution is prepared by mixing 16.8 parts water, 28.9 parts sodium silicate (28.7 wt % SiO$_2$, 8.9 wt % Na$_2$O, 62.4 wt % H$_2$O) 0.05 parts 50% wt NaOH and 0.08 parts Daxad 27 (W. R. Grace). An acid solution is prepared by adding 1 part aluminum sulfate (17.2% wt Al$_2$O$_3$) to 12.6 parts H$_2$O and then adding 2.9 parts H$_2$SO$_4$ and 1.7 parts NaCl. These solutions are mixed in an agitated vessel and 1.2 parts NaCl and 0.8 parts H$_2$O were added to the gel. An organic solution containing 2.9 parts tetrabutylammonium bromide and 4.2 parts water was then added to the gel and thoroughly blended. The mixture is heated to 93.3° C. and held for 234 hours with a high level of agitation. At the end of this period the temperature was raised to 137.8° C. for 72 hours to complete crystallization.

The crystallized product is washed and dried and then identified as 105% crystallinity ZSM-11 by X-ray diffraction with the following chemical analysis:

|  | % wt. |
| --- | --- |
| Al$_2$O$_3$ | 1.99 |
| SiO$_2$ | 92.0 |
| Na | 0.60 |
| N | 0.65 |
| C | 9.95 |

The washed and dried zeolite product is calcined in flowing N$_2$ for 3 hours at 537.8° C. then ion exchanged with 1N NH$_4$NO$_3$ solution (5 parts NH$_4$NO$_3$ solution/1 part zeolite) for 1 hour at ambient temperature and dried at about 121° C. The silica to alumina mole ratio of the resultant zeolite is 78.

EXAMPLE 2

Small crystal size Cs-ZSM-11 may be prepared by the ion-exchange of NH$_4$-ZSM-11 of Example 1 with a cesium chloride solution containing a small amount of cesium hydroxide, resulting in an ammonium removal of approximately 99%.

DIAGNOSTIC EVALUATIONS

In order to develop a meaningful diagnostic evaluation of zeolites that could be used for predicting separation properties, the selective sorption properties of various zeolites under competitive conditions are examined. In general, two or more substrates are dissolved in an inert (non-sorbable) solvent, i.e. one having a critical dimension greater than 6.8 Angstroms, and the relative decrease in concentration of each sorbate due to addition of various zeolites is measured. The sorbates to be used are the purest forms available commercially. Inert non-sorbable solvents useful herein include:

1,3,5-trimethylbenzene (M=mesitylene)
1,3,5-triisopropylbenzene (T,) and
1,3-di(trifluoromethyl)benzene (D).

In a typical experiment, 2 grams of a solution containing two sorbates (2.5% by weight each) in the inert solvent is added directly to 1 gram of a zeolite contained in a vial. This mixture, which is occasionally shaken or stirred at room temperature, is sampled periodically for changes in substrate concentrations. These samples are analyzed by vapor phase chromatography and are compared to the original solution analyzed in the identical manner. The selectivity is calculated by the formula defined hereinabove.

EXAMPLES 3 TO 9

Examples 3 to 9 are directed to the preferential sorption of a linear paraffin over a branched isomeric paraffin. The linear paraffin in these examples is n-hexane and the branched paraffin is 3-methylpentane. The zeolite employed in Example 3 was prepared in accordance with the procedure of Example 1.

As shown in Table I, linear n-hexane is selectively sorbed over branched 3-methylpentane by HZSM-5 and HZSM-11, in contrast to the lower selectivities exhibited by HZSM-12 and Mordenite.

If one were to compare the selective sorption of n-hexane relative to 3-methylpentane under the competitive equilibrium, non-kinetic conditions carried out herein, and examine the sorption properties of each hydrocarbon individually over a particular zeolite, the results would be very illuminating.

If these hydrocarbons are individually examined for sorption characteristics, the sorption capacity for n-hexane is almost twice that of 3-methylpentane at room temperature; at higher temperatures and consequently lower pore fillings (60 mg/gram), both isomers appear to sorb to a similar extent. The competitive results, on the other hand, demonstrate selectivity factors greater than 10 in favor of n-hexane, even at partial pore fillings.

EXAMPLES 10 TO 12

These examples illustrate the preferential sorption of a lesser branched olefin (heptene-1) over a more highly branched-isomeric olefin (4,4-dimethyl-1-pentane) by the use of ZSM zeolites and modifications. As clearly shown in Table II, the use of cations such as cesium enhance the selective preference for the lesser substituted hydrocarbons.

TABLE I
SELECTIVE SORPTION OF A LINEAR PARAFFIN OVER A BRANCHED PARAFFIN

| Ex. No. | Zeolite | Time hrs. | Inert Solvent | % A$^{(c)}$ Sorbed | % B$^{(d)}$ Sorbed | Total Sorbed mg/g | Selectivity A/B |
|---|---|---|---|---|---|---|---|
| 3 | HZSM-11 | 1 | T | 88 | 35 | 62 | 14 |
| 4 | NH$_4$—ZSM-12 | 2 | T | 49 | 26 | 30 | 2.7 |
| 5 | HZSM-12 | 1 | T | 57 | 39 | 48 | 2.1 |
| 6 | Dealum. H—Zeolon | 1 | T | 42 | 52 | 24 | 0.7 |
| 7 | HZSM-5$^{(a)}$ | 3 | M | 83 | 19 | 48 | 21 |
| 8 | HZSM-5$^{(a)}$ | 17 | M | 84 | 24 | 51 | 17 |
| 9 | HZSM-5$^{(b)}$ | .1 | M | 85 | 32 | 56 | 12 |

$^{(a)}$small crystal size
$^{(b)}$large crystal size
$^{(c)}$A = n-hexane
$^{(d)}$B = 3-methylpentane

TABLE II
SELECTIVE SORPTION OF A LINEAR OLEFIN OVER A BRANCHED OLEFIN

| Ex. No. | Zeolite | Time hrs. | Inert Solvent | % A$^{(1)}$ Sorbed | % B$^{(2)}$ Sorbed | Total Sorbed mg/g | Selectivity A/B |
|---|---|---|---|---|---|---|---|
| 10 | HZSM-5 | 18 | M | 69 | 30$^{(3)}$ | 95 | 5.3 |
| 11 | Cs—ZSM-5 | 0.2 | M | 52 | 5 | 60 | 20 |
| 12 | Cs—ZSM-5 | 72 | M | 50 | 11 | 64 | 8 |

$^{(1)}$A = heptene -1
$^{(2)}$B = 4,4-dimethylpentene-1
$^{(3)}$Extensive isomerization of both olefins occurred.

Lesser branched aromatic compounds are selectively sorbed in favor of a more highly branched aromatic compound, for instance, n-pentylbenzene vs. 1-methylbutylbenzene and v. 1-ethylpropylbenzene. Oil may be fractionated at temperatures below 150° C. Linear n-paraffins n-C$_{17}$ and n-C$_{18}$ are selectively sorbed from isoparaffins, namely isoprenoids phytane and pristane. Hetero-substituted aliphatic compounds that are sorbed selectively include haloalkanes, such as 1-chloroheptane or the like.

Linear aliphatic hydrocarbons may be sorbed selectively from cyclo aliphatic compounds. For instance, C$_6$ to C$_{18}$ n-alkanes are sorbed individually and cyclohexane is also individually sorbed; however, in admixture the linear aliphatics are sorbed preferentially. Table III shows the relative sorption properties of ZSM-5 and ZSM-11 for selective sorption of a C$_6$ linear paraffin from a solution containing a C$_8$ non-linear hydrocarbon.

TABLE III
SELECTIVE SORPTION OF PARAFFINS FROM SOLUTION

| Ex. No. | Zeolite | Solv.$^a$ | Si/Al$_2$ | Time Hrs. | % n-Nonane Sorbed | % p-Xylene Sorbed | Total Sorbed mg/g | Select Nonane Xylene |
|---|---|---|---|---|---|---|---|---|
| 13 | H—ZSM-5 | T | 62 | 4 | 72 | 3 | 56 | 82 |
| 14 | H—ZSM-5 | T | 62 | 27 | 74 | 5 | 59 | 57 |
| 15 | H—ZSM-5 | T | 62 | 20 | 83 | 10 | 73 | 43 |
| 16 | H—ZSM-5 | D | 62 | 20 | 63 | 4 | 66 | 45 |
| 17 | H—ZSM-5 | H | 62 | 70 | 47 | 3 | 50 | 30 |
| 18 | H—ZSM-11 | T | 78 | 6 | 98 | 34 | 66 | 99 |
| 19 | H—ZSM-11 | T | 78 | 5 | 77 | 3 | 60 | 116 |
| 20 | H—ZSM-11 | T | 78 | 24 | 78 | 4 | 61 | 83 |

EXAMPLE 21

Selective sorption of mixed waxy paraffinic compounds from a feedstock containing a full range of paraffins is an effective use of ZSM-11 zeolites. For instance, an Arab Light Distillate (204°–343° C.) is passed over a highly siliceous zeolite in a column. The early fraction elutriating from the column is highly enricched in aromatics.

EXAMPLE 22

A vacuum gas oil (650° F.+) is passed over HZSM-11 zeolite prepared as in Example 1 at 140° C. in a column. The early fraction elutriating from the column is substantially enriched in aromatics, indicating selective sorption of the paraffinic components.

What is claimed is:

1. A process for selective separation of a linear paraffin compound in admixture with at least one branched paraffin compound, said compounds having a critical dimension of less than 6.8 Angstrom Units for sorption, which comprises contacting the mixture of paraffins with zeolite ZSM-11, said zeolite being characterized by a silica:alumina mole ratio of at least 12, to effect selective sorption of said linear paraffin by said zeolite.

2. The process of claim 1 wherein said paraffins are isomers.

3. The process of claim 1 wherein n-hexane is selectively sorbed from a solution containing methyl pentane.

4. The process of claim 3 wherein said zeolite comprises H-ZSM-11, having a Constraint Index of about 2 to 12.

5. A process for selective separation of a linear aliphatic compound in admixture with at least one branched aliphatic compound, said compounds having a critical dimension of less than 6.8 Angstrom Units for sorption, which comprises contacting the mixture of compounds with zeolite ZSM-11, said zeolite being characterized by a silica:alumina mole ratio of at least 12, to effect selective sorption of said linear compound by said zeolite.

6. The process of claim 5 wherein said compounds are paraffinic isomers, and the branched paraffins are methyl-substituted.

7. The process of claim 6 wherein said zeolite comprises H-ZSM-11 and said paraffin compounds comprise n-hexane and 3-methylpentane.

8. The process of claim 5 wherein hexene-1 is selectively sorbed from a solution containing methyl pentene.

* * * * *